(12) United States Patent
Wang et al.

(10) Patent No.: US 9,328,151 B2
(45) Date of Patent: May 3, 2016

(54) VIBRIO HARVEYI-SPECIFIC BINDING DOWN SYNDROME CELL ADHESION MOLECULE, METHOD FOR IDENTIFICATION THEREOF AND USE THEREOF

(71) Applicant: NATIONAL CHENG KUNG UNIVERSITY, Tainan (TW)

(72) Inventors: Han-Ching Wang, Tainan (TW); Hsin-Yi Hung, Tainan (TW); Tze-Hann Ng, Tainan (TW); Yi-An Chiang, Tainan (TW)

(73) Assignee: National Cheng Kung University, Tainan (TW)

( * ) Notice: Subject to any disclaimer, the term of this patent is extended or adjusted under 35 U.S.C. 154(b) by 63 days.

(21) Appl. No.: 14/054,977

(22) Filed: Oct. 16, 2013

(65) Prior Publication Data

US 2015/0044699 A1    Feb. 12, 2015

(30) Foreign Application Priority Data

Aug. 7, 2013  (TW) .............................. 102128338 A (51) Int. Cl.
*C07K 14/435* (2006.01)
*G01N 33/569* (2006.01)

(52) U.S. Cl.
CPC .... *C07K 14/43509* (2013.01); *G01N 33/56911* (2013.01); *G01N 2333/28* (2013.01)

(58) Field of Classification Search
None
See application file for complete search history.

(56) References Cited

PUBLICATIONS

Hung HY et al. Properties of Litopenaeus vannamei Dscam (LvDscam) isoforms related to specific pathogen recognition. 2013. Fish & Shellfish Immunology. 35:1272-1281.*

Ng TH et al. Review of Dscam-mediated immunity in shrimp and other arthropods. 2014. Developmental and Comparative Immunology. 46:129-138.*

Pope EC et al. Enhanced Cellular Immunity in Shrimp (*Litopenaeus vannamei*) after 'Vaccination'. 2011. PLoS One. 6(6): e20960. p. 1-7.*

Wang KC et al. RNAi knock-down of the Litopenaeus vannamei Toll gene (LvToll) significantly increases mortality and reduces bacterial clearance after challenge with Vibrio harveyi. 2010. Developmental and Comparative Immunology. 34:49-58.*

P. H. Chou, et al., "The putative invertebrate adaptive immune protein Litopenaeus vannamei Dscam (LvDscam) is the first reported Dscam to lack a transmembrane domain and cytoplasmic tail.", Dev. Comp. Immunol., 2009, vol. 33, No. 12, p. 1258-1267.

E. C. Pope et al., "Enhanced Cellular Immunity in Shrimp (*Litopenaeus vannamei*) after 'Vaccination'", PLoS One, 2011, vol. 6, No. 6, e20960.

B. E. Chen et al., "The Molecular Diversity of Dscam is Functionally Required for Neuronal Wiring Specificity in *Drosophila*", Cell, 2006, vol. 125, No. 3, p. 607-620.

* cited by examiner

*Primary Examiner* — Paul Holland
(74) *Attorney, Agent, or Firm* — Rosenberg, Klein & Lee (57) ABSTRACT

The present invention relates to a *Vibrio harveyi*-specific binding Dscam of shrimps, a method for identification thereof and a use thereof. Primarily, Dscam cDNAs are prepared from *V. harveyi*-challenged shrimps. A database is established with various Dscam isoforms therein by means of numerous cloning and sequencing. After a phylogenetic analysis, a plurality of candidate Dscam isoforms is selected. Each recombinant protein of candidate Dscam isoforms is expressed through an expression system. Finally, the binding affinity between *V. harveyi* and each recombinant protein of candidate Dscam isoforms is measured to further selection of a *V. harveyi*-specific binding Dscam and the amino acid sequence thereof. Accordingly, the Dscam can be specifically binding to *V. harveyi* for eliminating or reducing *V. harveyi*.

3 Claims, 7 Drawing Sheets

| Normal Dscam isoforms | | | V. harveyi-induced Dscam isoforms | | |
|---|---|---|---|---|---|
| S. | Ig2/Ig3[a] | Number of observed clones | S. | Ig2/Ig3[a] | Number of observed clones |
| N1[b] | 16/5 | 8 | V1 | 16/36 | 8 |
| N2[b] | 17/46 | 7 | V2[b] | 1/54 | 6 |
| N3 | 18/38 | 7 | V3 | 6/58 | 5 |
| N4 | 4/13 | 6 | V4 | 18/5 | 5 |
| N5 | 18/41 | 6 | V5[b] | 22/54 | 5 |
| N6 | 19/32 | 5 | V6 | 4/46 | 4 |
| N7 | 24/44 | 5 | V7 | 6/12 | 4 |
| N8 | 1/10 | 5 | V8 | 9/37 | 4 |
| N9 | 8/9 | 4 | V9 | 13/57 | 4 |
| N10 | 9/38 | 4 | V10 | 16/38 | 4 |
| N11 | 16/41 | 4 | | | |
| N12 | 17/5 | 4 | | | |
| N13 | 19/46 | 4 | | | |

VIBRIO HARVEYI-SPECIFIC BINDING DOWN SYNDROME CELL ADHESION MOLECULE, METHOD FOR IDENTIFICATION THEREOF AND USE THEREOF

BACKGROUND OF THE INVENTION

1. Field of the Invention

The present invention relates to a *Vibrio harveyi*-specific binding Down syndrome cell adhesion molecule (Dscam), a method for identification thereof and a use thereof. A Dscam selected from *V. harveyi*-challenged shrimps includes an amino acid of SEQ ID NO:1 specifically binding to *V. harveyi* to eliminate or reduce *V. harveyi* for purposes of substantially lowering pathogenic growth.

2. Description of Related Art

For almost a century, the supply from capture fisheries goes on a downward trend due to the worsening overfishing phenomenon. Therefore, aquaculture may be the primary source of supply of aquatic food in the future. Shrimp farming industry began to develop since the 1980s. However, a lack of professional training and management concepts of breeding biosecurity leads to serious outbreaks of shrimp infectious diseases, e.g. vibriosis, shrimp white spot syndrome or the like, resulting in the collapse of the global shrimp farming industry. *Vibrio harveyi* is the most important pathogen that causes *vibrio* infectious diseases to shrimps or other various aquatic organisms. In order to get rid of such a predicament, prevention and treatment of shrimp infectious diseases are imperative.

Up to now, non-specific antibiotic or non-hypervariable antimicrobial peptide (AMP) is mostly used to reduce water microflora and enhance shrimp immunity in prevention and treatment of shrimp infectious diseases. For instance, U.S. Pat. No. 7,670,836, issued on 2 Mar. 2010, disclosed an antimicrobial peptide, monodoncin, which is isolated and purified from *Penaeus monodon* and is capable of being mass produced by molecular cloning techniques in a heterologous expression system, such as yeast. Monodoncin demonstrates a wide range of bacteriostatic and bactericidal effects on G (−) and G (+) bacteria as well as fungicidal activities, and can be used with conventional antibiotics in a "cocktail therapy" to improve the therapeutic effects of the conventional antibiotics. However, the foregoing antibiotic and AMP lack the feature of identifying the pathogen specifically, so it is likely to cause imbalance of water microflora and shrimp health. Furthermore, excessive use of antibiotics could not merely lead shrimps to drug resistance easily, but also seriously affect food safety.

Besides, there are other ways to prevent aquatic animals from pathogens, such as U.S. Pat. No. 7,807,144, issued on 5 Oct. 2010, disclosed an oral vaccine that includes a multiple-cell organism for use as food for an aquatic animal (e.g., a fish or a shrimp) to be vaccinated, and a method of multiple-cell organism encapsulating a single-cell organism or an antigen, wherein the single-cell organism has been transformed to express a substance (including recombinant antigen, DNA, RNA and saccharide) that can resist to disease and/or induce an immune response in the aquatic animals for promotion of aquatic animal immunity. However, some disadvantages still exist in the US patent i.e. complicacy in preparation, difficulties to predict the realistic response after transferring the nucleic acid in different aquatic animals, insufficient uptake, weak delivery and degradation in the digestive tract of nucleic acids.

SUMMARY OF THE INVENTION

In view of the above-mentioned problems, the object of the present invention is to provide a Dscam selected from *V. harveyi*-challenged shrimps, including an amino acid of SEQ ID NO:1 for specifically binding to *V. harveyi*. Therefore, the Dscam can eliminate or reduce *V. harveyi* to substantially lower pathogenic growth of shrimps.

Disclosed herein is a *Vibrio harveyi*-specific binding Dscam, a method for identification thereof and a use thereof. The Dscam of shrimps comprises at least 85% sequence homology with SEQ ID NO:1, preferably at least 90% homology and more preferably at least 95% homology with SEQ ID NO:1. The method for identifying the *Vibrio harveyi*-specific binding Dscam of shrimps comprises: (A) preparing a Dscam cDNA selected from *V. harveyi*-challenged shrimps; (B) establishing a database with various Dscam isoforms therein by sequencing Dscam cDNA clones to conduct a phylogenetic analysis on similarity and emergence for selecting a plurality of candidate Dscam isoforms; (C) using an expression system to produce recombinant Dscam isoform proteins; and (D) investigating the binding affinity between *Vibrio harveyi* and the recombinant Dscam isoform proteins for selecting the *Vibrio harveyi*-specific binding Dscam, wherein the Dscam is a sequence consisting of Ig2 and Ig3 regions of isoform V5.

The use of *V. harveyi*-specific binding Dscam of shrimps is also revealed herein for specifically binding to *Vibrio harveyi* to eliminate or reduce *V. harveyi* to further decrease infection of shrimps with *V. harveyi*. The Dscam of shrimps can be used to manufacture shrimp feed, aquatic animal feed additives, water treatment agents, antimicrobial peptides, immune enhancers and so on. Therefore, it can achieve the goal for specifically suppressing the proliferation of *V. harveyi* without destroying other probiotics.

According to an embodiment of the present invention, the shrimp is selected from the group consisting of *Litopenaeus vannamei, Litopenaeus setiferus, Penaeus monodon, Litopenaeus duorarum, Litopenaeus stylirostris, Penaeus setiferus, Penaeus vannamei, Penaeus japonicus, Penaeus chinensis, Penaeus orientalis* and *Acetes chinensis*, wherein the best is selected from the *Litopenaeus vannamei*.

DETAILED DESCRIPTION OF THE PREFERRED EMBODIMENT

Through investigating the immune system of shrimps, the inventors found that the expression of the highly variable Down syndrome cell adhesion molecule (Dscam) is significantly increased after infected with pathogen. Moreover, Dscam is capable of specifically binding to pathogen. Therefore, the present inventors consider that Dscam may play a similar role in antibodies of the adaptive immune system and thus can be specific resistance to pathogen infection.

Figure 1:
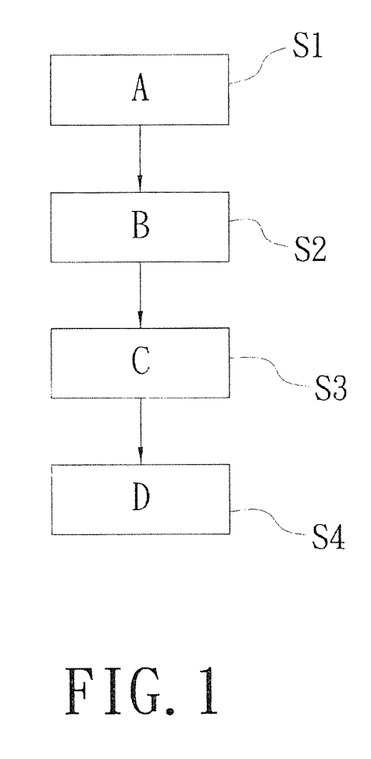
FIG. 1 is a flowchart for the identification of *Vibrio harveyi*-specific binding Dscam according to the present invention.

First, referring to FIG. 1, a flowchart for the identification of *Vibrio harveyi*-specific binding Dscam according to the present invention is disclosed. A method for identifying the *Vibrio harveyi*-specific binding Dscam of shrimps comprises the steps of:

(A) (S1) preparing a Dscam cDNA selected from *V. harveyi*-challenged shrimps;

(B) (S2) establishing a database with various Dscam isoforms therein by sequencing Dscam cDNA clones to conduct a phylogenetic analysis on similarity and emergence for selecting a plurality of candidate Dscam isoforms;

(C) (S3) using an expression system to produce recombinant Dscam isoform proteins; and (D) (S4) investigating the binding affinity between *Vibrio harveyi* and the recombinant Dscam isoform proteins for selecting the *Vibrio harveyi*-specific binding Dscam, wherein the Dscam is a sequence consisting of Ig2 and Ig3 regions of isoform V5.

A *Vibrio harveyi*-specific binding Dscam of shrimps comprises at least 85% sequence homology with SEQ ID NO:1, preferably at least 90% homology, such as at least 95% homology or 100% homology with SEQ ID NO:1.

A use of *V. harveyi*-specific binding Dscam of shrimps is also revealed herein for specifically binding to *Vibrio harveyi* to eliminate or reduce *V. harveyi* to further decrease infection of shrimps with *V. harveyi*. The Dscam of shrimps can be further used to manufacture shrimp feed, aquatic animal feed additives, water treatment agents, antimicrobial peptides, immune enhancers and so on. Therefore, it can achieve the goal for specifically suppressing the proliferation of *V. harveyi* without destroying other probiotics.

It is worth mention that the referred shrimps in the present invention can be (but not limited to) as followings: *Litopenaeus vannamei, Litopenaeus setiferus, Penaeus monodon, Litopenaeus duorarum, Litopenaeus stylirostris, Penaeus setiferus, Penaeus vannamei, Penaeus japonicus, Penaeus chinensis, Penaeus orientalis* and *Acetes chinensis*.

Hereinafter, an exemplary embodiment of the present invention will be described in detail with reference to the accompanying drawings.

EXAMPLE 1

Acquiring Dscams from *V. harveyi*-Challenged Shrimps

Pacific white shrimps (*Litopenaeus vannamei*) (body weight: 10-13 g) were obtained from a local shrimp culture farm. Before the experiments, the shrimps were maintained in a water tank system at salinity of 30 ppm at 25-27° C. for 3 days.

*V. harveyi* was isolated and used to prepare an inoculum. Briefly, the *V. harveyi* isolated from diseased *L. vannamei* was identified by using an API-20E commercial kit to sequence the *Vibrio* pathogenic gene hemolysin. Once its identity was confirmed, the *V. harveyi* was cultured overnight in a Tryptic Soy Broth (TSB). After centrifugation of the broth, the supernatant was removed and the pellet was re-suspended in sterilized seawater (SSW) and used as the bacterial inoculum.

For the *V. harveyi* challenge group, shrimp were injected intramuscularly with aforementioned *V. harveyi* inoculum ($8.3 \times 10^3$ colony forming unit/g shrimp). Shrimp in the control group were injected with SSW only. At different time points (0, 1, 3, 12, 18, 24, 36, 48 and 72 h post infection), four pooled hemocyte samples were collected from each group (3 shrimp in each pooled sample). Total RNAs were extracted with TRIzol reagent (Invitrogen) and first-strand cDNAs were generated using random hexanucleotide primer (100 μg/ml) and M-MLV Reverse Transcriptase (Promega). Dscam expression was determined by RT-qPCR using the primer set Ds-Real-4573F (SEQ ID NO:2)/Ds-Real-4635R (SEQ ID NO:3), and for this assay, $2^{-\Delta\Delta Ct}$ was calculated.

EXAMPLE 2

Establishment of a Database with Various Dscam Isoforms Therein and Phylogeny Analysis To further investigate the Ig2 and Ig3 exon diversity in the isoform populations of *V. harveyi*-challenged shrimp, at 36 hours post induction (hpi), 3 pooled samples were collected from each group and subjected to RT-PCR using the primer set F16 (SEQ ID NO:4)/R8 (SEQ ID NO:5) in order to amplify partial Dscam hemocyte cDNA fragments containing the Ig1-9 domains. Individual colonies (n=30) containing the variable Ig2-Ig3 region were randomly selected from each pooled sample, cloned and successfully sequenced using the forward primer F24 (SEQ ID NO:6). The resulting sequences of a total of 90 clones from each group were aligned using Genedoc software. The redundancy of each Ig2-Ig3 combination in each group was quantified, and the top 10 combinations were subjected to a cluster analysis using the MrBayes program. Briefly, the database with various Dscam isoforms therein is established by numerous sequencing Dscam cDNA clones and the top 10 redundancy of Dscam isoforms (including N1~N10 and V1~V10) are selected for further phylogenetic analysis.

EXAMPLE 3

Using an Expression System to Produce Recombinant Dscam Isoform Proteins

For the binding assay, an *E. coli* expression system is used to produce recombinant Dscam isoform proteins. The Dscam Ig1-Ig4 region of each selected isoform was amplified from the corresponding plasmid using the primer set LvD-NdeI-1F (SEQ ID NO:7)/LvD-NotI-1026R(SEQ ID NO:8). The Ig1-Ig4 partial sequence fragments were digested by NdeI/NotI and then ligated to the pET-28b(+) vector. The recombinant plasmids were transformed into *Escherichia coli* BL21 (DE3) CodonPlus-RIL cells (Stratagene). The expression of the recombinant proteins was induced by isopropylthio-β-galactoside (IPTG) according to manufacturer's instructions.

To purify the recombinant proteins from *E. coli* BL21 (DE3), the IPTG-induced bacteria were suspended in binding buffer (5 mM imidazole, 0.5M NaCl, 20 mM Tris-HCl, pH7.9) with 0.1% lysozyme and kept on ice for 30 mins. After centrifugation, the bacterial pellets were suspended in binding buffer containing 8M urea and incubated at 4° C. overnight under gentle agitation. The supernatant was collected by centrifugation and subjected to Ni-NTA affinity chromatography (QIAGEN). The recombinant protein was then eluted with elution buffer (1× binding buffer containing 8M urea and 250 mM imidazole). After the elution buffer was replaced by 1×PBS using a PD-10 desalting column (GE Healthcare), the recombinant protein fractions were concentrated using 30 kDa ultrafiltration membranes (MILLIPORE) and checked by SDS-PAGE and Western blotting. Then Bradford assays (Bio-Rad) were used to measure the protein concentrations of each recombinant isoform. To confirm the protein concentrations, purified samples (1 μg of each isoform) were subjected to another 12% SDS-PAGE and stained with Coomassie Brilliant Blue R-250 or transferred to PVDF membranes for Western blotting using rabbit anti-His Ig polyclonal antibody as a primary antibody.

EXAMPLE 4

Investigating the Binding Affinity Between *Vibrio harveyi* and the Recombinant Dscam Isoform Proteins The purified, quantified recombinant Dscam isoform proteins (rDscam) as described above were then used in the pathogen binding assay, including in vitro bacteria binding assays and virus binding assay.

In Vitro Bacteria Binding Assays 10 ml of culture broth containing Gram-negative (G(−)) bacteria, *E. coli* or *V. harveyi*, and Gram-positive (G(+)) bacteria, *Staphylococcus aureus*, were collected when OD600 reached 1.6 (*E. coli* and *S. aureus* are the bacteria common in water). After inactivating the bacteria at 65° C. for 30 min, each sample was pelleted by centrifugation at 4500×g for 10 min, washed three times with 1×PBS, and suspended in 1×PBS (10 ml). For the assay, each rDscam isoform (1 μg) was mixed with 100 μl bacterial solution and PBS was added to a final volume of 130 μl. Recombinant EGFP protein (rEGFP) (1 μg) was used as a negative control.

After washing with PBS, the samples were centrifuged at 8,000×g for 5 minutes at 4° C. and the supernatant was removed. The pellet was resuspended in 100 μl 0.1 M carbonate/bicarbonate buffer, pH 9.6, and coated onto a 96-well polystyrene plate for 2 h at 37° C. To detect bound rDscam isoforms, the wells were blocked with blocking buffer (2% BSA in PBST) and then incubated with anti-His antibody for 1 h at room temperature.

The 96-well plates were then washed with PBST and goat anti-rabbit HRP-conjugated secondary antibody was added and allowed to react for 1 h. To develop the signal, enzyme activity was started by the addition of freshly prepared 3,3',5,5'-tetramethylbenzidine (TMB) substrate (Sigma) for 10 min and stopped by the addition of the stop solution (1N HCl). Finally, the absorbance of each well was measured at a wavelength of 450 nm. All samples were analyzed in duplicate.

In Vitro Virus Binding Assay

For the virus binding assay, the protocol was similar to the bacteria binding assays described above. Briefly, each rDscam isoform (1 μg) was mixed with 2 μg of purified white spot syndrome virus (WSSV) virions, and PBS was added to a final volume of 100 μl. rEGFP protein (1 μg) was used as a negative control. After incubation at 4° C. overnight, the samples were washed in PBS and centrifuged at 15,000×g for 30 minutes at 4° C. The pellet was then re-suspended with 100 μl of carbonate/bicarbonate buffer, pH 9.6, and coated onto 96 well polystyrene microtitre plates for 2 h at 37° C. To detect the bound rDscam isoforms, the wells were then reacted with primary and secondary antibodies, washed and developed as described above for the in vitro bacteria binding assays.

Results

Result 1: In the Dscam isoforms that are most highly induced by *V. harveyi*, five out of the top ten share similar sequences.

Figure 2:
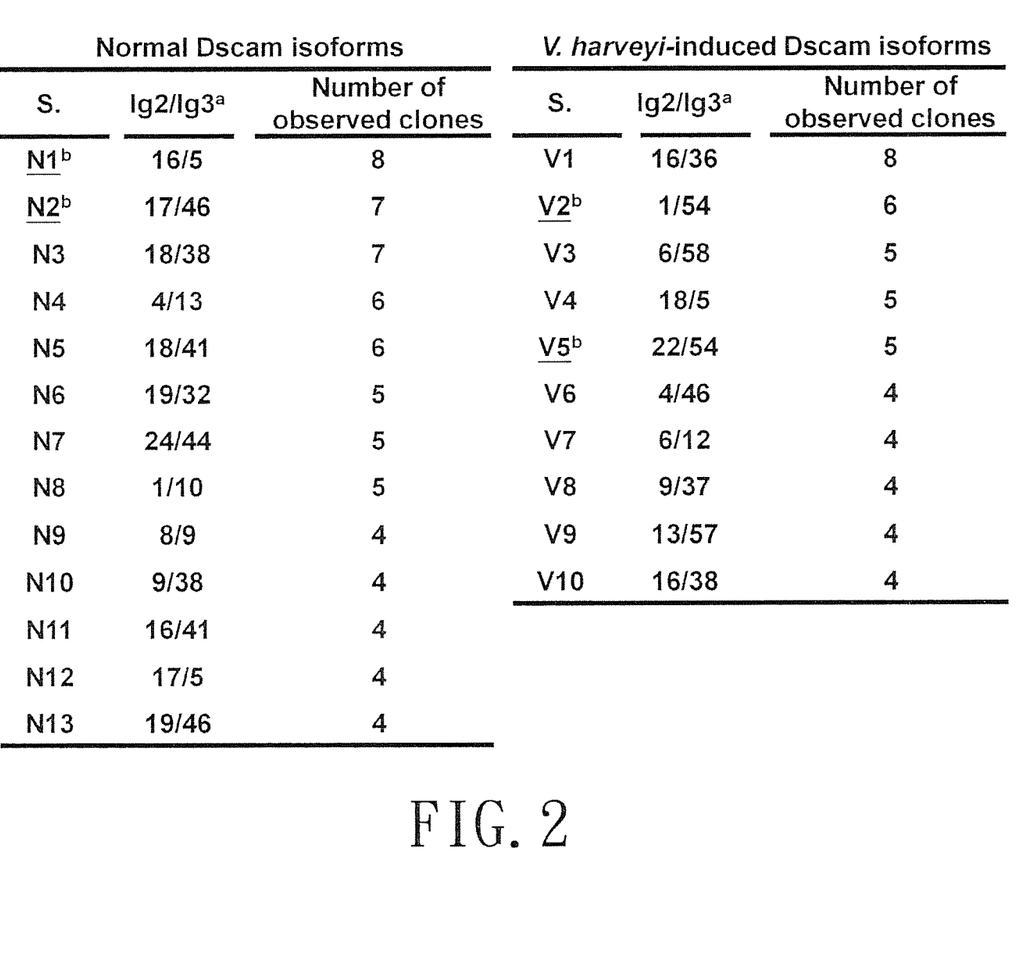
FIG. 2 is a diagram showing various Ig2-Ig3 combinations of Dscam isoforms and statistics of emergence according to the present invention.
Figure 3:
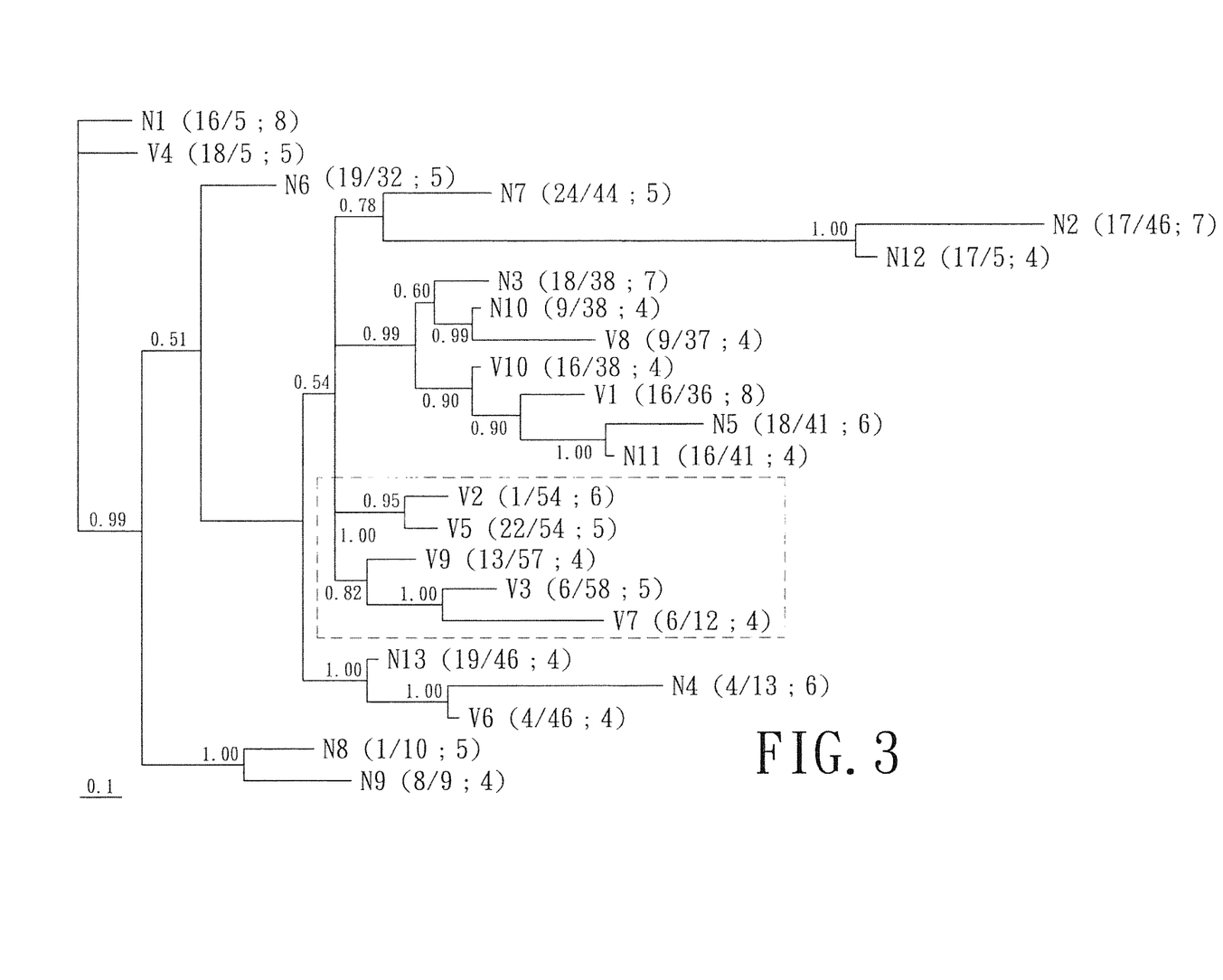
FIG. 3 is a diagram showing the phylogenetic analysis on Dscam isoforms according to the present invention.
Figure 4A:
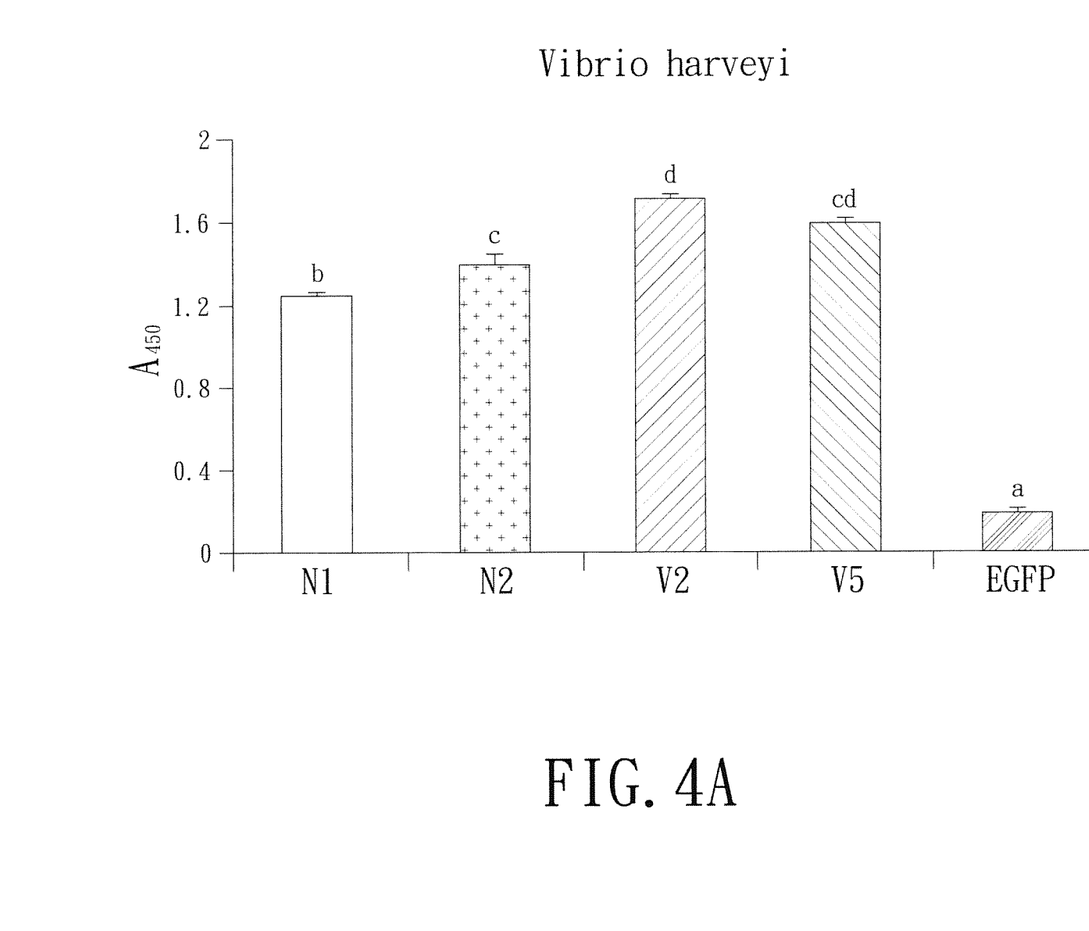
FIG. 4A is a diagram showing the binding affinity assays of recombinant Dscam isoform proteins to *V. harveyi*.
Figure 4B:
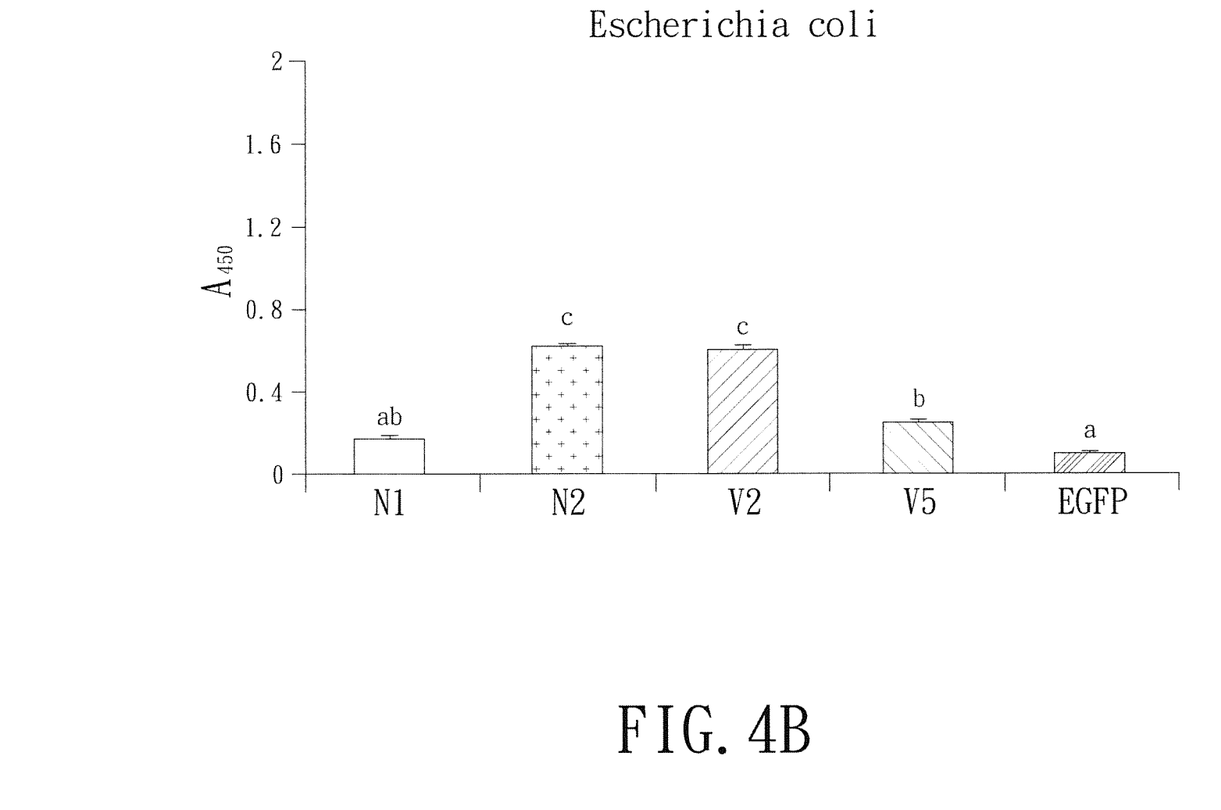
FIG. 4B is a diagram showing the binding affinity assays of recombinant Dscam isoform proteins to *E. coli*.
Figure 4C:
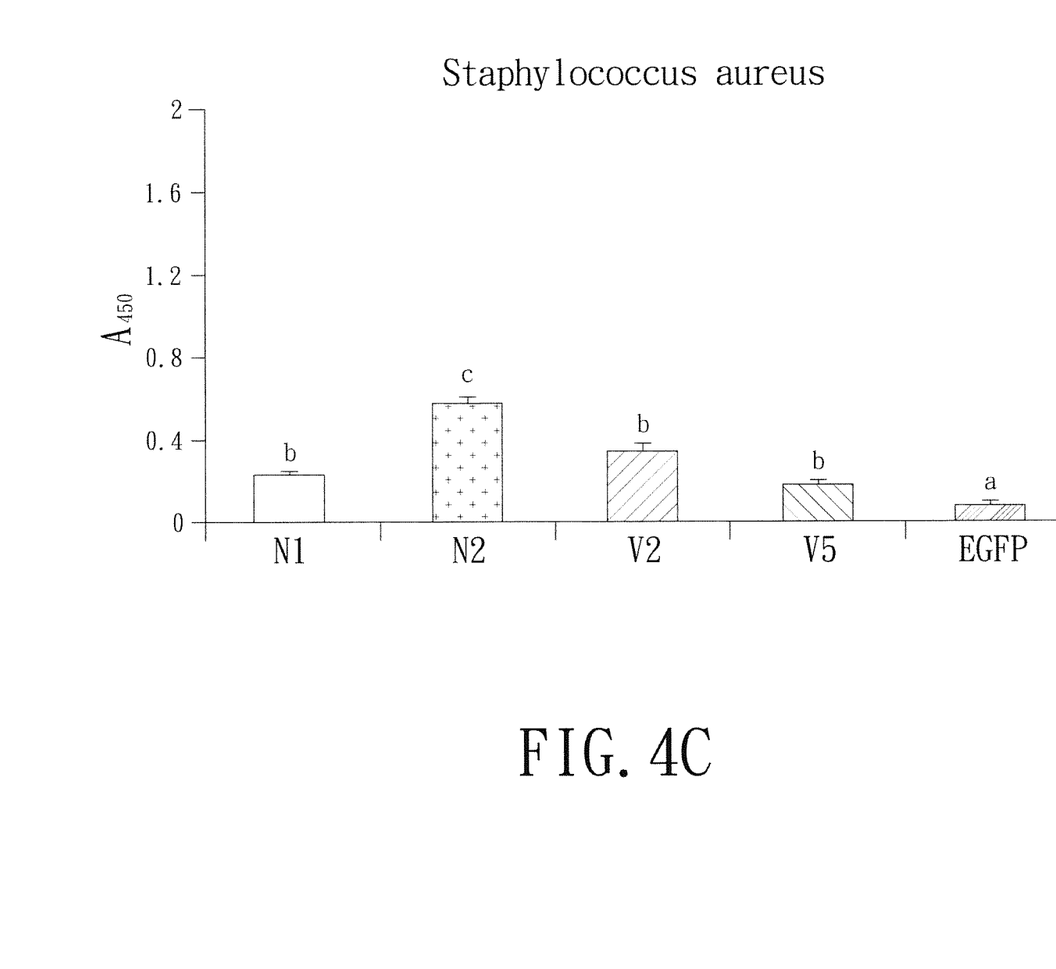
FIG. 4C is a diagram showing the binding affinity assays of recombinant Dscam isoform proteins to *S. aureus*.
Figure 4D:
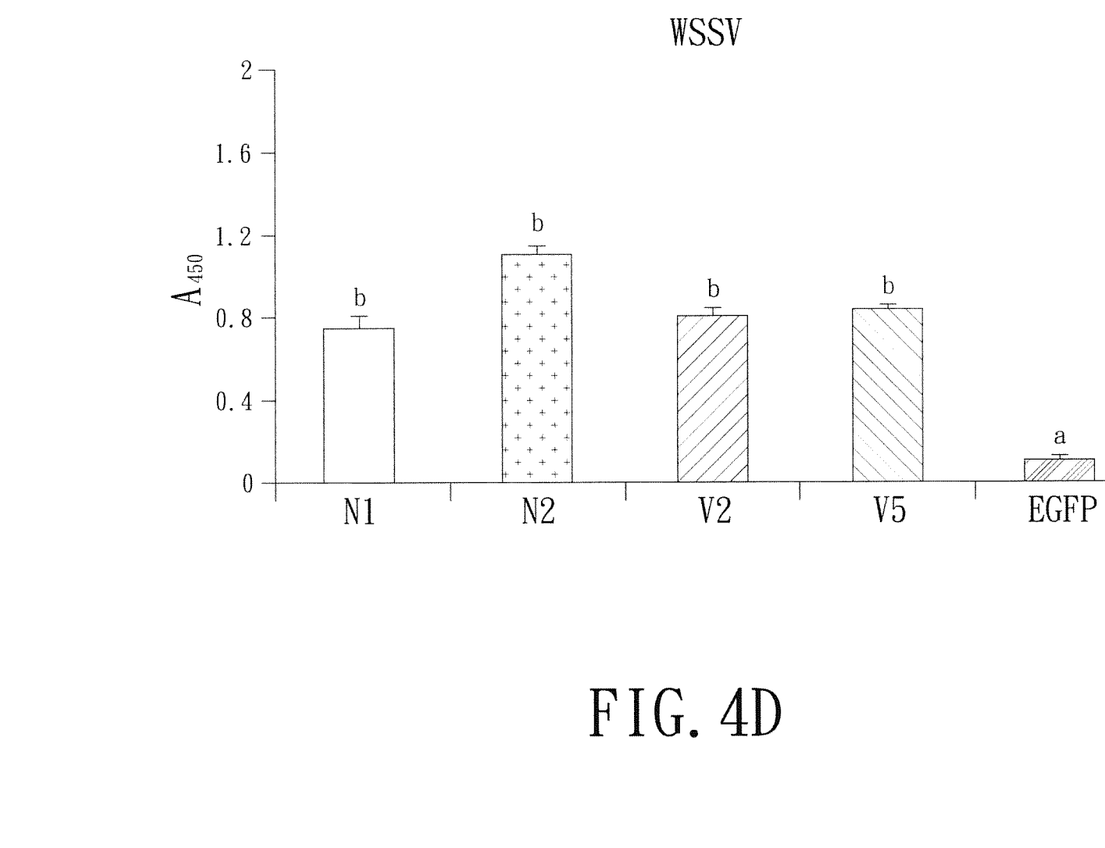
FIG. 4D is a diagram showing the binding affinity assays of recombinant Dscam isoform proteins to WSSV.

To identify Dscam Ig2-Ig3 combinations that were induced by *V. harveyi*, we collected hemocyte samples at 36 hpi from the SSW- and *V. harveyi*-injected shrimp described above. From each group, after amplification with the primer set F16 (SEQ ID NO:4)/R8 (SEQ ID NO:5)), a total of 90 clones from 3 pooled samples were randomly selected and sequenced. As shown in FIG. 2, the top thirteen most highly expressed isoforms (normal Dscam isoforms) in the SSW shrimp were considered to be non-*V. harveyi*-induced isoforms (N). A top ten list of the most highly expressed *V. harveyi*-induced (V) isoforms was similarly compiled, except that this list excluded any isoform that was also found among the non-*V. harveyi*-induced isoforms. The mentioned lowercase letter "a" in FIG. 2 represents the name of each Dscam isoforms, and "b" represents Dscam isoforms participated in binding affinity of pathogens. Using Bayesian inference methods, a clustering analysis of the Ig2-Ig3 amino sequences of these 23 isoforms showed that five *V. harveyi*-induced isoforms (V2, V5, V9, V3 and V7) (as shown in dotted box section of FIG. 3) formed separate clades from the other non-*V. harveyi*-induced and *V. harveyi*-induced isoforms and had much similarity to each other.

Result 2: Among *V. harveyi*-induced Dscam isoforms, V5 appears to be the most specific for *V. harveyi*.

To further investigate whether the Ig2/Ig3 combinations within the Glade bind more specifically to *V. harveyi* than other, normal (N) isoforms, 4 isoforms (N1, N2, V2, V5) were selected to express recombinant proteins for a series of pathogen binding assays.

Referring to FIG. 4, diagrams showing the binding affinity assay of recombinant Dscam isoform proteins are disclosed. In the *V. harveyi* binding assay as shown in FIG. 4A, recombinant proteins from all four of these isoforms showed a significantly stronger binding ability than the EGFP (negative control) protein. In the *E. coli* binding assay as shown in FIG. 4B, all binding abilities were relatively low, but the isoforms N2 and V2 showed a significantly stronger binding ability than N1, V5 and the EGFP protein. In the *S. aureus* (which is non-lethal to shrimp) binding assay as shown in FIG. 4C, the binding abilities were also relatively low compared to the *V. harveyi* binding assay. Isoform N2 produced the strongest signal while no significant difference was found between N1, V2 and V5. In a binding assay with the shrimp viral pathogen WSSV as shown in FIG. 4D, there was no significant difference between the four isoforms, all of which showed significantly greater binding activity than the EGFP protein control. The mentioned lowercase letters "a", "b", "c" and "d" in the histogram represent the comparison of the difference between the various isoforms in binding affinity. For instance, in FIG. 4A, V5 belongs to "cd" which represents that V5 has no significant difference of binding affinity between N2 (belong to "c" group) and V2 (belong to "d" group), whereas comparing V5 and N1, which belong to "cd" and "b" respectively, are representatives of significant difference of the binding affinity between two isoforms. Briefly, the binding affinities labeled the same English lowercase letter represent belonging to the same group and thus there is no significant difference between each other. In contrast, labeled different English lowercase letters represents a significant difference between each other.

In summary, among recombinant Dscam isoform proteins of *L. vannamei*, V5 appears to be the most specific for binding to *V. harveyi*. Therefore, it can be used to manufacture shrimp feed, aquatic animal feed additives, water treatment agent, antimicrobial peptides, immune enhancer and so on, and thus it can be added to food or feed or living environment of shrimps. Accordingly, it can achieve the goal for specifically suppressing the proliferation of *V. harveyi* without destroying other probiotics.

According to the above description, in comparison with the traditional technique, a *Vibrio harveyi*-specific binding Dscam, a method for identification thereof and a use thereof according to the present invention has the advantages as following:

1. The present invention selected a *V. harveyi*-specific binding Dscam of shrimp from numerous Dscam isoforms, which can be mass production and applied to farm water treatment in the future for reducing *V. harveyi* infection. Accordingly, the Dscam will be with a great benefit to the aquaculture industry.
2. The Dscam can be specifically binding to *V. harveyi* as well as solve the problems, i.e. failing distinction between good bacteria and bad bacteria of antibiotics or antimicrobial peptides leading to imbalance of water aquatic bacteria and shrimp health. Furthermore, the Dscam also solves the problems of that immune enhancer can only slightly increase shrimp immunity without coping with the excessive proliferation of pathogens.
3. The present invention decreases *V. harveyi* infection in shrimps or diminishes the proliferation of *V. harveyi* in water, which can reduce the outbreak of vibriosis and lower people's concerns about food safety when eating shrimps.

---

SEQUENCE LISTING

<160> NUMBER OF SEQ ID NOS: 8

<210> SEQ ID NO 1
<211> LENGTH: 153
<212> TYPE: PRT
<213> ORGANISM: Litopenaeus vannamei

<400> SEQUENCE: 1

```
Val Arg Ala Val Val Pro Gln Ala Tyr Leu Ile Asp Val Ser Met Glu
1               5                   10                  15

Asn Val Ile Arg Gly Asn Ser Ala Ile Leu Lys Cys Asn Ile Pro Ser
            20                  25                  30

Phe Val Ala Asp Phe Val Ser Val Gln Ala Trp Val Thr Asp Lys Gly
        35                  40                  45

Asp Asn Tyr Tyr Pro Ser Asp Arg Tyr Asp Gly Lys Tyr Leu Val Leu
    50                  55                  60

Pro Ser Gly Glu Leu His Ile Arg Ser Val Ser Ser Glu Asp Gly Phe
65                  70                  75                  80

Lys Ser Tyr Lys Cys Arg Thr Val His Arg Leu Thr Gln Glu Thr Arg
                85                  90                  95

Leu Ser Ala Thr Ala Gly Arg Leu Val Ile Ser Asp Pro Ala Gly Thr
            100                 105                 110

Ser Ala Pro Ser Leu Pro Ser Lys Glu Lys His Phe Thr Asp Val Lys
        115                 120                 125

Glu Arg Gly Ser Ser Val Ala Leu Phe Cys Ser Val Gln Ala Ser Pro
    130                 135                 140

Val Pro Gln Phe Arg Trp Phe Lys Val
145                 150
```

<210> SEQ ID NO 2
<211> LENGTH: 20
<212> TYPE: DNA
<213> ORGANISM: Artificial sequence
<220> FEATURE:
<223> OTHER INFORMATION: Primer-Oligonucleotide

<400> SEQUENCE: 2
acaagccaag gcaccagact                                          20

<210> SEQ ID NO 3
<211> LENGTH: 20
<212> TYPE: DNA
<213> ORGANISM: Artificial sequence
<220> FEATURE:
<223> OTHER INFORMATION: Primer-Oligonucleotide

<400> SEQUENCE: 3

-continued

```
<210> SEQ ID NO 4
<211> LENGTH: 18
<212> TYPE: DNA
<213> ORGANISM: Artificial sequence
<220> FEATURE:
<223> OTHER INFORMATION: Primer-oligonucleotide

<400> SEQUENCE: 4
atgggcacta cctatatg                                                       18

<210> SEQ ID NO 5
<211> LENGTH: 20
<212> TYPE: DNA
<213> ORGANISM: Artificial sequence
<220> FEATURE:
<223> OTHER INFORMATION: Primer-Oligonucleotide

<400> SEQUENCE: 5
gtagttgctg ggcggagatc                                                     20

<210> SEQ ID NO 6
<211> LENGTH: 18
<212> TYPE: DNA
<213> ORGANISM: Artificial sequence
<220> FEATURE:
<223> OTHER INFORMATION: Primer-Oligonucleotide

<400> SEQUENCE: 6
ctgatcttcc ctcccttc                                                       18

<210> SEQ ID NO 7
<211> LENGTH: 23
<212> TYPE: DNA
<213> ORGANISM: Artificial sequence
<220> FEATURE:
<223> OTHER INFORMATION: Primer-Oligonucleotide

<400> SEQUENCE: 7
cccatatggg cactacctat atg                                                 23

<210> SEQ ID NO 8
<211> LENGTH: 28
<212> TYPE: DNA
<213> ORGANISM: Artificial sequence
<220> FEATURE:
<223> OTHER INFORMATION: Primer-Oligonucleotide

<400> SEQUENCE: 8
ccgcggccgc aacagtctga accttggg                                            28
```

(first line of continued table: `gttgcctgtt gggctcactt    20`)

What is claimed is:

1. A *Vibrio harveyi*-specific binding Down syndrome cell adhesion molecule (Dscam) of shrimp consisting of the amino acid sequence of SEQ ID NO:1.

2. A method for reducing *Vibrio harveyi* infection in shrimp comprising contacting said shrimp with the *Vibrio harveyi*-specific binding Dscam of shrimp of claim 1, wherein said *Vibrio harveyi* infection is reduced relative to shrimp not contacted with said *Vibrio harveyi*-specific binding Dscam of shrimp of claim 1.

3. A composition comprising the *Vibrio harveyi*-specific binding Dscam of shrimp of claim 1, wherein said composition is selected from the group consisting of shrimp feed, aquatic animal feed additives, water treatment agents, antimicrobial peptides and immune enhancers.

* * * * *